United States Patent [19]

Tomoyasu et al.

[11] Patent Number: 4,958,128

[45] Date of Patent: Sep. 18, 1990

[54] METHOD OF EXAMINING AN INSIDE SURFACE-COATED METALLIC PIPE AND APPARATUS

[75] Inventors: Takaharu Tomoyasu; Kanji Miyamoto, both of Ichihara, Japan

[73] Assignee: Mitsui Petrochemical Industries, Ltd., Tokyo, Japan

[21] Appl. No.: 439,705

[22] Filed: Nov. 21, 1989

[30] Foreign Application Priority Data

Nov. 22, 1988 [JP] Japan .................... 63-295345

[51] Int. Cl.⁵ .............. B61B 13/08; G01N 27/02
[52] U.S. Cl. .................... 324/559; 73/40.5 R
[58] Field of Search ............ 73/150, 40.5 R; 324/557, 559

[56] References Cited

U.S. PATENT DOCUMENTS

| | | | |
|---|---|---|---|
| 2,573,815 | 11/1951 | Smith | 324/559 X |
| 3,253,217 | 5/1966 | Voltmann | 324/559 X |
| 4,050,384 | 9/1977 | Chapman | 73/40.5 R X |
| 4,244,296 | 1/1981 | Vertut | 73/40.5 R X |

FOREIGN PATENT DOCUMENTS

| | | | |
|---|---|---|---|
| 0030659 | 3/1981 | Japan | 324/559 |
| 0785709 | 12/1980 | U.S.S.R. | 324/559 |

Primary Examiner—Daniel M. Yasich

[57] ABSTRACT

A process for detecting a poorly coated portion of an inside surface of a pipe coated with an insulation coat comprises the steps of providing a plurality of pigs on a conductor at predetermined intervals, preparing a running element provided with many electrode needles radially between these pigs, inserting the running element into the pipe while measuring the insulation resistance between the pipe and the conductor, and moving the running element inside the pipe by adjusting the pressure inside the pipe. From the above process, when the electrode needles make contact with a poorly coated portion of the inside surface while the running element is moving inside the pipe, the insulation resistance between the pipe and the conductor is decreased, thereby enabling easy detection of the presence of a poorly coated portion and its position.

5 Claims, 2 Drawing Sheets

METHOD OF EXAMINING AN INSIDE SURFACE-COATED METALLIC PIPE AND APPARATUS

BACKGROUND OF THE INVENTION

The present invention relates to a method of examining the coat condition of an inside surface-coated metallic pipe and to an apparatus used for the examination.

In recent years, as a measure to counter the aging of water supply pipes and water drain pipes, a technique to coat the inside surface of pipes by injecting epoxy resin by using air so that they can withstand reuse after the corroded layers of a pipe are removed and ground, has been adopted.

However, since an object distributing pipe system generally forms a complicated system having many branches and bendings, a problem has arisen, namely, certain unpainted portions remain depending on the setting of painting conditions such as the amount of paint.

For this reason, when an uncoated portion remains, it must be detected and coated again. For detecting it, the following methods have been adopted in the past.

First, there is a method in which a fiber scope having flexibility is inserted into the inside of a pipe from the gateway of the pipe, and by visually checking the wall surface inside the pipe, the presence of defects is detected.

Second, there is a method in which an electrode is provided in the tip of a conductor and inserted into the inside of a pipe, then the coat condition is checked by utilizing the instantaneous electric discharge phenomenon.

Third, as shown in FIG. 4, there is a method in which the pipe 41 which is coated with 45 is filled with an electrolytic solution 42, one end of the insulation meter 43 being connected to the pipe 41 on one hand, and the other end of the pipe 43 being connected to the electrode bar 44 inserted into the pipe 41. According to this method, when a defect exists on the coat 45, since the electrolytic solution makes direct contact with the pipe 41, insulation resistance is decreased, thereby enabling the defect to be detected.

In the first method described above, however, in the case of a small 20A (JIS standard) sized pipe or thereabouts, only a scope having about four bendings or less can be inserted. What is more, this operation requires a highly difficult technique. The length that the apparatus can detect is generally about 3 m. In recent years, an apparatus has been produced capable of measuring to the depth of 6 m. It is, however, very expensive, and there is room for improvements in its maneuverability.

In the second method, an examination inside a bent pipe rather than a straight pipe is difficult since the means for inserting an electrode into an intricately bent pipe has not been developed.

In the third method, since the entire pipe 41 must be filled with the electrolytic solution 42, the preparation on a large scale is required. Furthermore, though in the third method, a defect can be detected by a change in an indication of the insulation meter 43, specifying the defect's location is difficult, so such a method cannot be put into practical use.

The present invention has been devised in light of the foregoing problems. It is a technical objective of the present invention to provide a method of examining the coat condition of an inside surface-coated metallic pipe and an apparatus for use in such a method, in which coat defects can be detected easily and reliably even in an intricately bent pipe, and its position can be determined.

SUMMARY OF THE INVENTION

To solve the above-described technical problems, in the present invention the method as described below is adopted. In this method the poorly coated portion of the inside surface of an insulation coated pipe is detected.

A plurality of pigs are provided on a conductor at predetermined intervals. Next, a running element provided with a number of electrode needles radially on the conductor between the pigs is provided. Next, this running element is inserted into the pipe. By the use of air, a difference of pressure is caused to occur between the front and back of this running element, thereby causing the running element to move in the pipe.

As a result of the above, when the electrode needle contacts a defectively coated portion of the inside surface of the pipe while the running element is moving in the pipe, the insulation resistance between the pipe and the conductor is decreased, thereby enabling the presence of a poorly coated portion to be detected.

The apparatus for detecting a poorly coated portion of an inside surface of an insulation coated pipe is arranged in the following manner.

A plurality of pigs are provided on a conductor at predetermined intervals. A number of electrode needles are radially provided on the conductor positioned between these pigs, and a running element is formed. A pressure adjusting apparatus for causing a difference of pressure inside a pipe is connected to the pipe into which the running element is to be inserted, forming an apparatus for examining the coat condition of the inside surface of the metallic pipe.

The above construction enables the running element to be easily moved to a desired position by decreasing the pressure in the destination pipe and increasing the pressure in the other pipes depending on the direction in which the running element is to be guided.

Since the electrode needles of the running element project radially, these electrode needles move while contacting the inside insulation coated surface, and when there is a poorly coated portion, the electrode needles directly or proximately contact the pipe. This contact decreases the insulation resistance greatly, so a defective coat can be detected. By measuring the length of the movement of the running element, that is, the length of the extension of the conductor in the pipe, the position of a defect can be located easily.

According to the present invention, as described above, this running element can be smoothly inserted into a winding pipe since the running element is arranged in such a way that its electrode needles are provided radially on a conductor. Since a difference of pressure is caused to occur between the front and back of the running element in the pipe to cause it to move in the pipe, a predetermined branch pipe can be checked easily in a distributing pipe having many branch pipes by opening and closing the ends of a multi-branched pipe. Therefore recovery of a running element is easy, and a highly difficult technique for the operation is not required.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 1 is a perspective view of a running element;

FIG. 2 is a side elevational view of an essential portion of FIG. 1;

FIG. 3 is a side view illustrating the example of operation of an apparatus for examining the coat condition of an inside surface-coated metallic pipe.

DESCRIPTION OF THE PREFERRED EMBODIMENTS OF THE INVENTION

Figure 1:
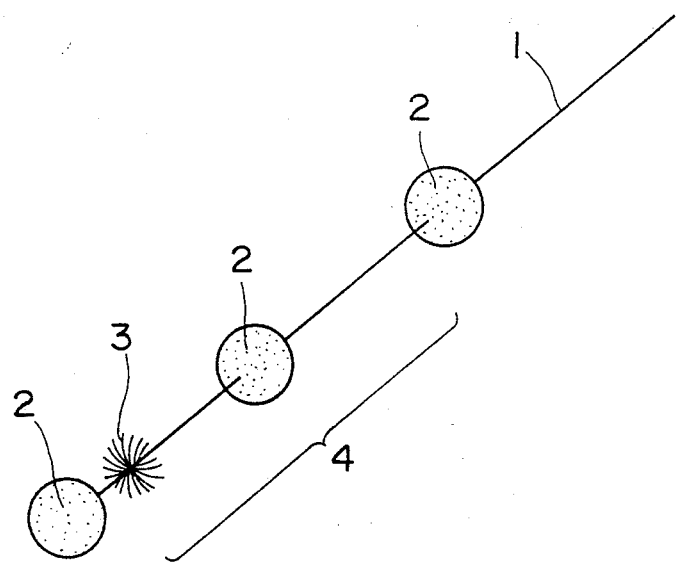
FIGS. 1 to 3 show the embodiments of the present invention.
Figure 2:
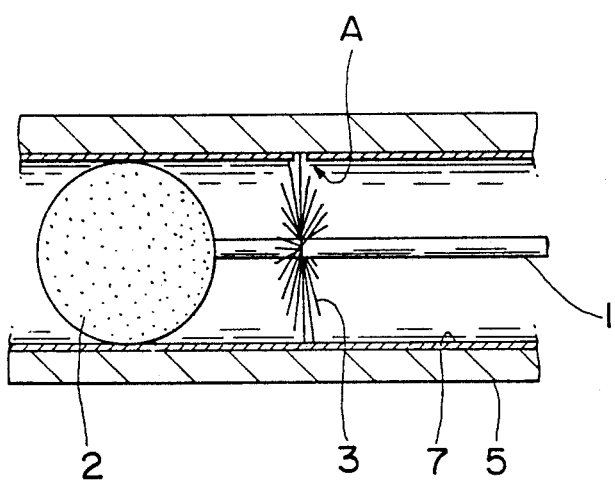

Each of the embodiments of the present invention will be described below in detail.

The embodiments of the present invention will now be described with reference to the drawings 1 to 3.

This device is used to detect a poorly coated portion of an inside surface of a pipe 5 coated with an insulation coat 7, and three pigs 2 are provided on the tip section of the flexible conductor 1 at predetermined intervals. These pigs 2 are made of spherical sponges, and are molded smaller than the internal size of the pipe 5. The distance between these pigs 2 is set to 50 cm.

A number of electrode needles 3 are radially provided on the conductor 1 positioned between the pigs 2 perpendicularly to the axis.

Figure 3:
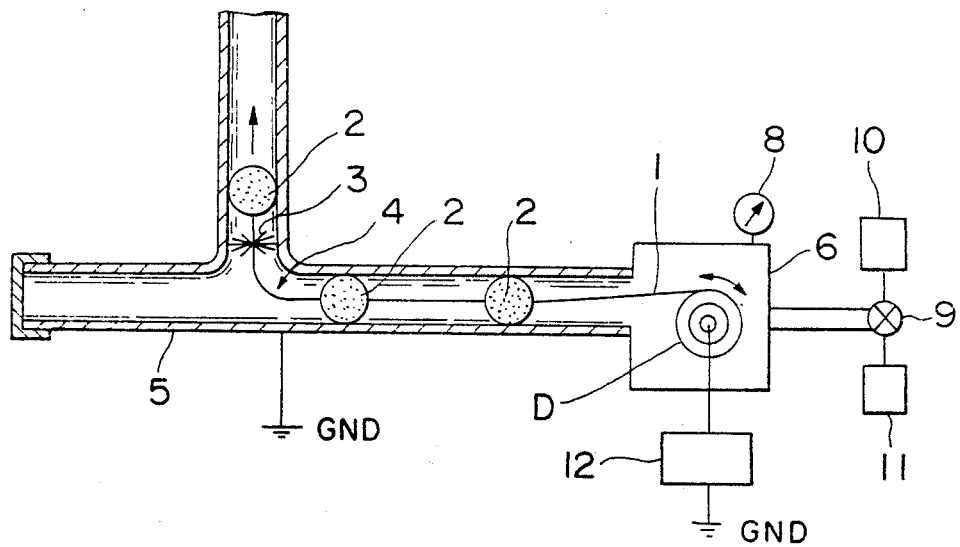
Figure 4:
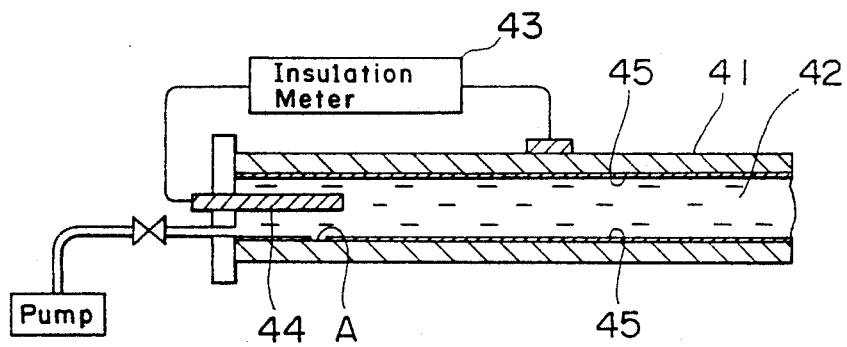
FIG. 4 is a drawing illustrating a conventional apparatus.

As shown in FIG. 3, this electrode needle 3 is formed by a flexible thin conductor so that it does not damage the inside surface of a pipe. The back end section of the conductor 1 is wound on the drum D. The length of the extent of the conductor, that is, the length of the movement of the running element 4 is displayed. A pressure adjusting apparatus 6 for generating a pressure difference inside the pipe 5 is connected to the pipe 5 through which the running element 4 constructed as described above is to be inserted, and its state of pressure can be read by a pressure gauge 8. An insulation mete is connected outside the pipe between the conductor 1 and the pipe 5, and can measure the resistance value while providing an electric potential of 5 to 1000 V. A pressure increasing apparatus 10 and a pressure decreasing apparatus 11 are connected to the pressure adjusting apparatus 6 via a three-way valve 9.

The example of operation will be explained below.

The insulation coat 7 is coated in advance to the inside of the pipe 5. A running element 4 is inserted into the pipe 5. In due course a pressure of 1 kg/cm² is applied in the back of this running element 4 to cause it to move. In this case, the pipes except the one to which the element is guided are closed tight, and the running element 4 is guided to move to a predetermined pipe.

As described above, while the running element is caused to move, the insulation resistance between the conductor 1 and the pipe 5 is monitored by the insulation resistance meter 12 outside the pipe at all times. When the inside surface coat is in an excellent condition, the insulation resistance meter 12 shows a relatively high value.

On the other hand, in the case of a defective or poor surface coat, when the electrode needles 3 are contacted with the poorly coated poriton A, the insulation resistance between the pipe 5 and the conductor 1 is decreased considerably, the value of which is displayed on the insulation resistance meter 12. The position of the running element 4 is detected by the state of the pressure difference in the pipe 5 at this time, that is, the path the running element 4 moved and the length of the extension of the conductor 1 from the drum D, namely, the length the running element 4 moved. The defective portion A can therefore be located very easily from outside a pipe.

In the present embodiment, since the pigs are positioned between the bendings of a pipe, the frictional force in the bending section of the conductor 1 is softened. Therefore, no possibility that the coat surface is damaged exists. The size of the pigs 2 are set to the thinnest pipe through which they pass. Accordingly, it can pass without being caught halfway. When the pulling force of the conductor 1 is weak, the number of pigs 2 should be increased accordingly.

Upon completion of the examination, it can be easily recovered by generating a negative pressure of 200 mmHg or thereabouts by the pressure adjusting apparatus 6.

Since a plurality of pigs 2 are applied with a pressure and caused to move, a force is not concentrated on a specific position, so the insulation coat 7 is not damaged.

An example of operation at a typical "T"-shape pipe is shown in FIG. 3. However, it goes without saying that the invention is not limited to the present embodiment, but a more intricate path can similarly be checked. The distance between the pigs 2 can be set accordingly depending on the use from 10 cm to 5 m. It should preferably be set 5 to 30 times that of the diameter of a pipe. The pigs 2 can also be formed by plastic balls. The pressure to be applied inside a pipe can be appropriately set between 0.1 to 4 kg/cm². It is needless to say that the running element 4 can be guided to a desired position by decreasing the pressure inside the pipe to which it is guided as needed.

The criterion for judging whether the coat condition of an inside surface is good or bad differs according to the use of the pipe system. Detecting what degree of thickness of a coat is a defective coat differs from case to case. It can be dealt with a method of measuring the electric potential applied between the conductor 1 and the pipe 5 and the insulation resistance therebetween.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. In a process for detecting a poorly coated portion of an inside surface of a pipe coated with an insulation coat, a method of examining the coat condition of an inside surface of a metal pipe, comprising the steps of;

providing a plurality of pigs on a conductor at predetermined intervals;

preparing a running element provided radially with a number of electrode needles on said conductor between said pigs;

inserting this running element into said pipe;

causing a difference in pressure to generate using air in the front and back of the running element to move the running element inside said pipe; and detecting a decrease in insulation resistance between said pipe and said conductor caused by the contact of said electrode needles with the poorly coated portion of the inside surface of said pipe, thereby detecting the presence of a poorly coated portion.

2. The method of examining the coat condition of an inside surface coated metal pipe as claimed in claim 1, whereby a poorly coated portion in a pipe is located by the length of the movement of said running element and the state of the pressure difference in a pipe.

3. An apparatus for detecting a poorly coated portion of an inside surface of a metal pipe coated with insulation coat, comprising:

a plurality of pigs provided on a conductor at predetermined intervals;

a running element provided with a plurality of electrode needles extending radially on said conductor and positioned between the plurality of pigs; and a pressure adjusting apparatus for generating a pressure difference in front of and back of said running element inside said pipe, said pressure adjusting apparatus being connected to the pipe into which the running element is to be inserted.

4. The apparatus for examining the coat condition of an inside surface-coated metal pipe as claimed in claim 3, wherein said pigs are formed by spherical balls.

5. The apparatus for examining the coat condition of an inside surface-coated metal pipe as claimed in claim 4, wherein the back end of said conductor is wound on a drum placed outside the pipe, the position of said running element inside the pipe is detected by using the length of the extension of the conductor from this drum and the state of the pressure difference inside said pipe, thereby locating the position of a defect.

* * * * *